United States Patent
Okuyama

(12)
(10) Patent No.: US 6,171,575 B1
(45) Date of Patent: Jan. 9, 2001

(54) METHOD OF RADIOISOTOPIC ASSESSMENT OF THE INTEGRITY AND FUNCTION OF THE NOSE-BRAIN BARRIER

(76) Inventor: Shinichi Okuyama, 4-4-5 Kamo, Izumi-ku, Sendai 981-3122 (JP)

( * ) Notice: Under 35 U.S.C. 154(b), the term of this patent shall be extended for 0 days.

(21) Appl. No.: 09/057,366

(22) Filed: Apr. 6, 1998

(51) Int. Cl.$^7$ .......................... A61K 51/00; A61M 36/14
(52) U.S. Cl. ................ 424/1.13; 424/1.33; 424/1.37; 424/9.4; 424/1.11
(58) Field of Search ................... 424/1.11, 1.13, 424/1.21, 1.33, 1.37, 1.65, 9.1, 9.2, 9.3, 9.4; 119/9, 6, 823, 824; 536/53; 514/54, 415; 562/516; 530/400; 548/339.1; 423/583, 584

(56) References Cited

U.S. PATENT DOCUMENTS 5,725,852 * 3/1998 Igari et al. ........................ 424/85.7

OTHER PUBLICATIONS

Author: Shinichi Okuyama, Title: "The First Attempt at Radioisotopic evaluation of the Intergrity of the Nose–Brain Barrier" Apr. 18, 1997, Life Sciences, vol. 60, No. 21, pp. 1881–1884.
Author: Brian J. Balin et al., Title: "Avenues for Entry of Peripherally Administered Protein to The Central Nervous System in Mouse, Rat, and Squirrel, Monkey", *The Journal of Comparative Neurology,* vol. 251, 1986, pp. 260–280.
Author: Richard M. Kream et al., Title: "Olfactory Marker Protein: Turnover and Transport in Normal" *The Journal of Neuroscience,* vol. 4, No. 3, and Regenerating Neurons, Mar. 1984, pp. 868–879.

Author: Eigi Matsushima, "Olfactory Dysfunction of Dementia of Alzheimer Type", *J. Yonago Med. Assoc.,* vol. 42, 1991, pp. 120–127.
Author: Daniel P. Perl et al., "Uptake of Aluminium into Central Nervous System Along Nasal–Olfactory Pathways" *The Lancet,* 1987, pp. 1028.
Author: Eugene Roberts, "Alzheimer's Disease May Begin in the Nose and May Be Caused by Aluminosilicates", *Neurobiology of Aging,* vol. 7, 1986, pp. 561–567.
Author: A.H. Tomlinson et al., "Herpes Simplexencephalitis", *Journal of the Neurological Sciences,* vol. 60, 1983, pp. 473–484.
Author: M. Yamagishi et al., "Definitive Diagnosis of Alzheimer's Disease Using Olfactory Mucosal Biopsy", *Proceedings of Symposium on Testing and Olfactory Functions,* 1992, pp. 365–368.

\* cited by examiner

*Primary Examiner*—Dameron Jones

(57) ABSTRACT

A radioisotopic assessment of the integrity of the nose-brain barrier was performed on an anosmic patient by spraying an aliquot of a mixture of 99mTc-DTPA and hyaluronidase onto the olfactory mucosa with the patient's head positioned vertically and subsequently measuring the cerebral radioactivity. A significant rise in cerebral radioactivity was observed 5 minutes after introduction of the radioisotope. This simple technique will aid in assessing olfactory impairment from selected etiologies and also in testing the integrity of the nose-brain barrier. In view of the study of diseases such as viral encephalitis and Alzheimer's disease and others, the clinical implication of this method cannot be overemphasized. This principle may also facilitate developing novel pharmaceuticals for some brain diseases along with brain scintigraphy of novel modality.

7 Claims, 2 Drawing Sheets

US 6,171,575 B1

METHOD OF RADIOISOTOPIC ASSESSMENT OF THE INTEGRITY AND FUNCTION OF THE NOSE-BRAIN BARRIER

BACKGROUND OF THE INVENTION

The olfactory system possesses certain peculiarities: (i) The olfactory mucosa plugs the cribriform openings of the skull base; and (ii) The olfactory receptor cells connect themselves to neural cells in the olfactory bulb by passing their nerve fibers through these openings (1). Therefore, this mucosa functions as the nose-brain barrier (hereinafter designated as NBB). NBB's disintegration may result from a variety of pathological changes (categories I and II), leading to penetration of toxic chemicals and microorganisms into the brain system. Category I: Loss of the plugging integrity: (a) mucosal inflammation; and (b) degeneration and/or loss of the constituent olfactory receptor cells, supporting cells or basal cells. Category II: Morbid afferent transmission through the olfactory nerve fibers: (c) transmission of toxic chemicals; and possibly (d) transmission of viral particles.

The NBB's integrity may be of crucial importance in the etiology of influenzal encephalitis, Alzheimer's disease (Roberts 1986; Perl and Good 1987; Matsushima 1991; Yamagishi et al. 1992), and other diseases. The present study is the first attempt to develop a novel radioisotopic technique for detection of NBB disintegration.

It may help developing novel medicine for anesthesia and treatment of selected brain diseases.

DETAILED DESCRIPTION OF A PREFERRED EMBODIMENT

The method of the present invention includes mainly two steps:

(1) Introduction of the radiopharmaceutical onto the NBB
An example of the preparation of radiopharmaceuticals can be as follows: aliquots of 99mTc-diethylenetriaminepenta-acetic acid (99mTc-DTPA) prescribed -for standard renogrammatic analysis were mixed with hyaluronidase (100 biological units per ml of 99mTc-DTPA solution). The mixture was sprayed into the depth of the nose. One puff of the sprayer released 0.2 ml aliquots of the mixture containing 148 MBq of radioactivity. In order to protect the nasal mucosa, vinyl tubing was attached to the end of the nozzle of a sprayer. As the head of an examinee was positioned vertically, so as to allow the droplets to fall onto the olfactory mucosa, the examiner sprayed the mixture deep into one of the nostrils; and (2) Assessing the radioisotopic penetration across the NBB The radioisotopic spray side of the head of an examinee was placed against the detector collimator of a gamma camera for 10 minutes. Radioisotopic penetration was defined as the amount of radioactivity recorded in the regions of interest (ROIs) placed over the intracranial space adjoing the cribrijon lamine. The change of the recorded radioactivity in this ROI was analyzed along with that in a remote control brain area.

Test Result:

Test were performed to determine the penetration potential of radio-pharmaceuticals of $^{99m}$Tc-HMPAO and $^{99m}$Tc-DTPA.

Figure 1:
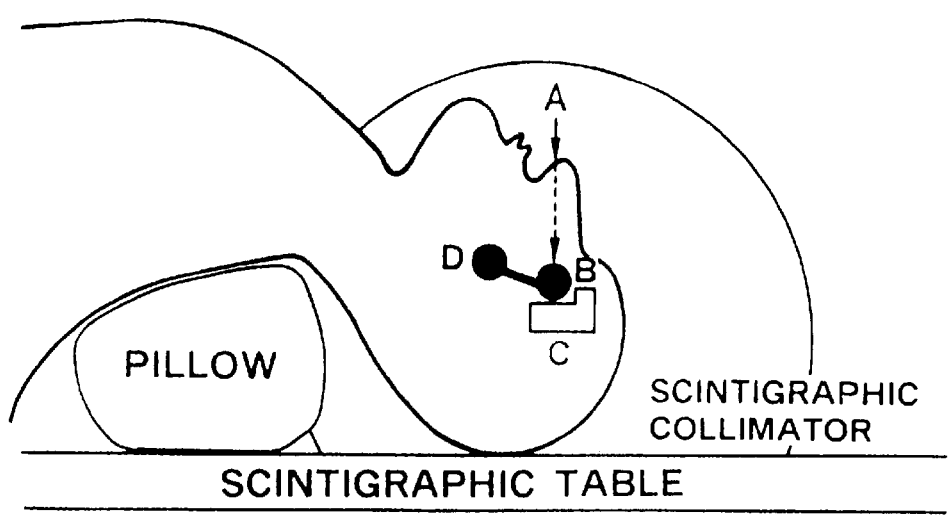
FIG. 1 shows how an examinee was prepared for testing the NBB's penetration. A. The radiopharmaceutical was sprayed deep into the nose through the nostril as the examinee laid on the scintigraphic table with the head placed in vertical position. B. The resultant radioactivity residing on the olfactory mucosa. C. The region of interest (ROI) placed just beneath the nose-brain barrier on the (cathode Ray Tube) so as to record the penetrating radioactivity. D. Pharyngeal radioactivity escaped from the olfactory pit.
Figure 2:
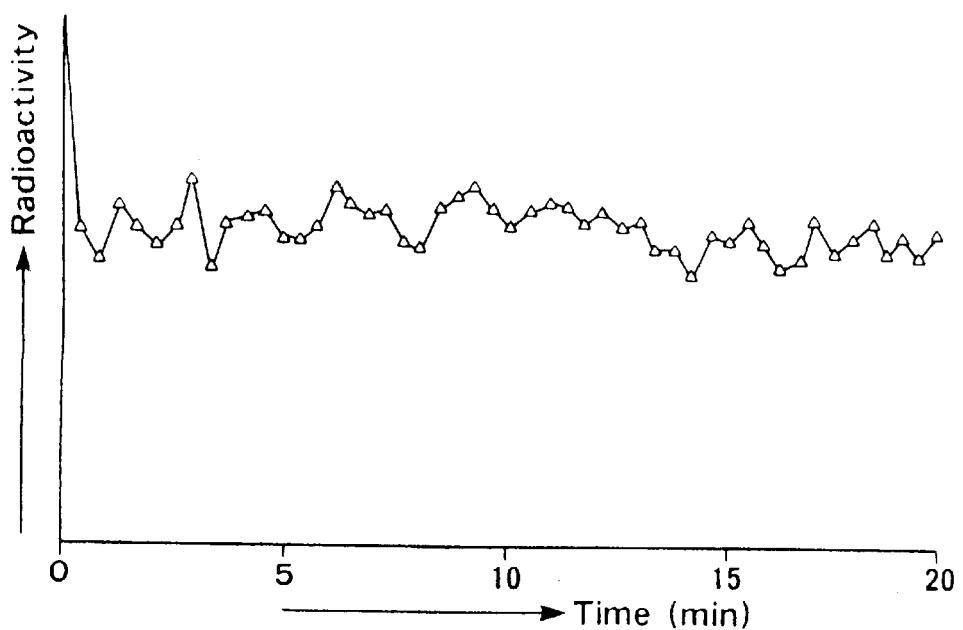
FIG. 2 shows the radioisotopic penetration across the NBB in a healthy control for $^{99m}$Tc-HMPAO. In particular, the figure shows radioactivity increase with time across the nose-brain barrier. (Closed circles: radioactivity recorded in the juxta-olfactory plate; open circles: radioactivity in the remote control brain site)

At least three typical tests were done: one for $^{99m}$-HMPAO on a 60-year-old healthy man, one for $^{99m}$-DTPA on the same healthy control, the third for $^{99m}$Tc-DTPA on a 67-year-old woman:

(1) No significant radioisotopic penetration was observable with $^{99m}$Tc-HMPAO in a 60-year-old healthy man (FIG. 2). The radioactivity of penetration was too small to yield scintigrams yet.

Figure 3:
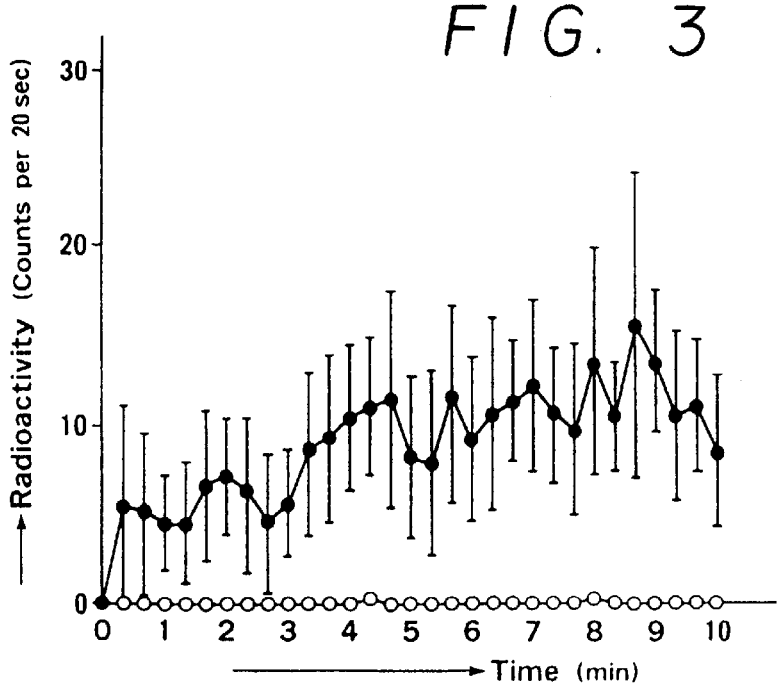
FIG. 3 shows the radioisotopic penetration across the NBB in a healthy control for $^{99m}$Tc-DTPA. Radioactivity in the brain juxta-cribriform plate increased but without any statistical significance.

(2) There was a tendency for the radiopharmaceutical to increase the NBB with $^{99m}$Tc-DTPA, although the change was statistically insignificant (FIG. 3). However, the radioactivity of penetration was too small to yield any scintigrams yet.

Figure 4:
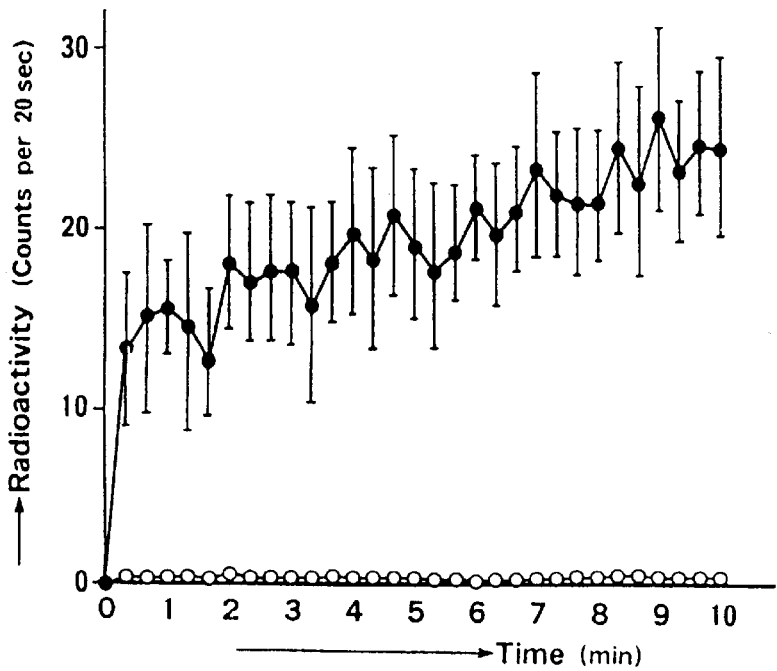
FIG. 4 shows the radioistopic penetration across the NBB in an anosmic patient for $^{99m}$Tc-DTPA. Radioactivity recorded in the brain juxta-cribriform plate increased significantly after 5 minutes of the radioistopic application.

(3) The 67-year-old woman, who had previously had the left breast irradiated for breast cancer, had developed anosmia 6 months before testing. Otological examination revealed that her olfactory dysfunction was limited to airborn scenting. Radioisotopic study indicated a significant increase in radioactivity in the juxta-cribriform lamional brain after 5 minutes of radio-isotopic introduction into the left nostril (FIG. 4). Thus, definite radioisotopic penetration across the NBB was achieved after 5 minutes.

This invention is a novel gamma ray-emitting radioisotopic method to study the olfactory function in human beings, revealing the definite appearance of radioactivity away from the site of application. This finding suggests that small but significant fractions of the radiopharmaceuticals sprayed onto the olfactory mucosa might have penetrated the NBB in an anosmic patient in a relatively short time. The radioactivity of penetration, however, was too small to yield legible scintigrams yet.

Physical porosity of the olfactory mucosa may occur when many of olfactory nerve cells are lost for one reason or another, including aging, and the subsequent regeneration is unable to compensate for the loss as in the case of Alzheimer's disease (Yamagishi et al. 1992), resulting in the disintegration of the so-called nose-brain barrier. Similar effects may be conceivable from "chemical porosity" as the result of inflammation-induced increased permeability.

The above observation may suggest an immediate clinical application of this technique to the study of several other diseases such as viral infections (e.g., influenza)(Tomlinson and Esiri 1983), Alzheimer's disease, and cases of toxic and/or inflammatory olfactory mucosal damage.

Although further refinement has to be made in terms of the efficacy of radiopharmaceutical penetration and specificity, the clinical importance of that principle cannot be overemphasized, especially in view of the development of potential drugs that would penetrate the NBB to reach the brain or the cerebrospinal space and that might help anesthesizing or treating selected regional and generalized brain disorders.

In this study, $^{99m}$Tc-DTPA was shown to pass the nose-brain barrier in human beings of olfactory pathology as well as healthy control. To the contrary, $^{99m}$Tc-HMPAO, an agent that circulates in the blood and passes through the blood-brain barrier, was shown not to pass the nose-brain barrier, however.

Additional potential radiopharmacological development is suggested by those studies with horseradish peroxidase (HRP)(Balin et al. 1986) and acidic protein extract from the olfactory tissues (olfactory marker protein, OMP) from the mouse, rat and squirrel monkeys (Kream and Margolis 1984), if they are properly labeled with radioisotopes.

These substances share a common property of passing and diffusing through the intercellular space: (1) DTPA spreads extracellularly as in the case of renogrammatic analysis and imaging and dynamic studies of the cerebrospinal fluid flow; (2) HRP localization studies with electron microscopy (Balin et al. 1986); and (3) detergent treatment of the nasal mucosa or the alike to denude the mucosal cell surfaces of fat (Kream and Margolis 1985).

Radioisotopic labeling can be expanded to those odor substances and especially, those neurotransmitters of low molecular weight such as serotonin, histamine, neurotensin, and melatonin, for they are accepted by receptors on the mucosal cell surface or pinocytosed, and probably transported through the mucosa to be released into the intracranial spaces. Then, the technique will be indispensable in selected clinical and pharmacological investigations.

$^{99m}$Tc-DTPA is water-soluble and its sprayed droplets are so large and heavy that they immediately precipitate onto the olfactory mucosa as it is sprayed in the vertical head position. If radiotracers consisting of finer droplets or dry fumes or completely volatile material are developed, the examinees and patients need not lie in the vertical head posture. Then, intranasal radioactive administration can be modified accordingly.

As the transition across the nose-brain barrier takes place in relatively short periods of time, radioactive labeling of the tracer substances can be expanded to labeling with cyclotron-produced positron-emitting elements as $^{11}$C, $^{13}$N, $^{15}$O and $^{18}$F. If combined with phosphorus, a magnetic spectroscopic application can also be feasible on the same principle as above.

At the moment, the radioactive penetration across the nose-brain barrier is too scanty to be scintigraphically imaged. However, on improvement by development of pharmaceuticals of greater affinity toward the olfactory mucosa and of greater penetration, the technique can be used for scintigraphic purposes of the brain, too. Then, usefulness of this invention cannot be overemphasized.

What is claimed is:

1. A method of radioisotopic evaluation of the penetrability of the nose-brain barrier comprising:

(i) spraying a radiopharmaceutical mixture onto the olfactory mucosa of a patient; and (ii) measuring cerebral penetration of the said radio pharmaceutical mixture.

2. The method according to claim 1, wherein the mixture comprises 100 units of hyaluronidase per milliliter of $^{99m}$Tc-DTPA.

3. The method according to claim 1, wherein the radiopharmaceutical is selected from the group consisting of horseradish peroxidase, olfactory marker protein, and a neuro-transmitter.

4. The method according to claim 1, further comprising positioning patient's head vertically in order to facilitate contact of the radiopharmaceutical mixture and olfactory mucosa.

5. The method according to claim 1, further comprising allowing the patient to change posture during administration of the radiopharmaceutical mixture and measurement of cerebral radioactivity.

6. The method according to claim 1, wherein cerebral penetration is assessed by determining the amount of radioactivity recorded in the regions of interest as a function of the juxta-cribriform laminal intracranial space.

7. The method according to claim 3, wherein the neurotransmitter is selected from the group consisting of serotonin, neurotensin, and melatonin.

* * * * *